United States Patent
Shotey et al.

(10) Patent No.: US 9,474,818 B1
(45) Date of Patent: Oct. 25, 2016

(54) AIR FRESHENER

(71) Applicant: Marcus J. Shotey, Scottsdale, AZ (US)

(72) Inventors: Marcus J. Shotey, Scottsdale, AZ (US); Scott Klug, Mesa, AZ (US)

(73) Assignee: Marcus J. Shotey, Scottsdale, AZ (US)

( * ) Notice: Subject to any disclaimer, the term of this patent is extended or adjusted under 35 U.S.C. 154(b) by 90 days.

(21) Appl. No.: 14/060,486

(22) Filed: Oct. 22, 2013

Related U.S. Application Data (60) Provisional application No. 61/716,706, filed on Oct. 22, 2012.

(51) Int. Cl.
*A61L 9/12* (2006.01)
*A61L 9/03* (2006.01)

(52) U.S. Cl.
CPC .................................... *A61L 9/032* (2013.01)

(58) Field of Classification Search
CPC .............................. A61L 9/122; A61L 9/032
USPC .......................................................... 422/124
See application file for complete search history.

(56) References Cited

U.S. PATENT DOCUMENTS

| | | | |
|---|---|---|---|
| 2,764,789 A * | 10/1956 | Zelenka | 422/124 |
| 4,064,203 A | 12/1977 | Cox | |
| 4,743,406 A | 5/1988 | Steiner et al. | |
| 4,762,275 A * | 8/1988 | Herbert et al. | 239/6 |
| D458,359 S | 6/2002 | Blanchette | |
| 6,581,915 B2 | 6/2003 | Bartsch et al. | |
| 7,618,151 B2 | 11/2009 | Abbondanzio et al. | |
| D660,950 S | 5/2012 | Finlay | |
| 8,178,048 B2 | 5/2012 | Zlotnik et al. | |
| 2001/0032000 A1 | 10/2001 | Dotan | |
| 2002/0158156 A1 * | 10/2002 | Joshi et al. | 239/590 |
| 2006/0039835 A1 * | 2/2006 | Nottingham | A61L 9/048 422/124 |
| 2006/0188238 A1 * | 8/2006 | Kent | 392/394 |
| 2009/0162253 A1 | 6/2009 | Porchia et al. | |
| 2009/0200393 A1 * | 8/2009 | Avelar | C11C 5/006 239/60 |
| 2010/0269826 A1 * | 10/2010 | Colombo et al. | 128/203.26 |
| 2010/0284783 A1 | 11/2010 | Lolmede | |
| 2011/0027124 A1 | 2/2011 | Albee et al. | |
| 2012/0312893 A1 * | 12/2012 | Santini et al. | 239/44 |

FOREIGN PATENT DOCUMENTS

WO    WO 2009053399 A2 *    4/2009

* cited by examiner

*Primary Examiner* — Kevin Joyner
*Assistant Examiner* — Holly Mull
(74) *Attorney, Agent, or Firm* — Booth Udall Fuller, PLC (57) ABSTRACT

An air freshener that includes a base and a reservoir is disclosed. The base includes a fan housed therein and one or more base openings extending through a sidewall of the base. The one or more base openings comprise an inlet opening and an outlet opening. The base also includes a coupling receiver positioned on an upper surface of the base. The reservoir includes a reservoir chamber configured to hold a scented liquid therein and an outlet. A coupling is typically coupled to the reservoir adjacent to the outlet and configured to removably couple to the coupling receiver. A filter is coupled to the coupling and in fluid communication with the reservoir chamber. The filter is positioned above the fan when the coupling is removably coupled to the coupling and allows the scented liquid to evaporate therefrom for dispersal through the base openings when the fan is activated.

15 Claims, 4 Drawing Sheets

AIR FRESHENER

CROSS REFERENCE TO RELATED APPLICATIONS

This document claims the benefit of the filing date of U.S. Provisional Patent Application 61/716,706, entitled "Air Freshener" to Shotey that was filed on Oct. 22, 2012, the contents of which are hereby incorporated by reference.

BACKGROUND

1. Technical Field

Aspects of this document relate generally to air fresheners.

2. Background Art

Air fresheners are known to come in a variety of forms, including chemical compositions that are activated by the air, fan operated devices that push or pull a scent into a room, and cardboard type materials that provide a scent in the air. The cardboard type materials are similar to an automotive tree air freshener that emits a scent and the freshener's effectiveness steadily decreases over time until the air freshener is nothing more than a decorative element. Chemical compositions may include gels or similar compositions that are absorbed into the air to mask any odors. Fan operated devices may be battery or outlet powered and typically push or pull air across a scented portion of the device and into the surrounding area. The scented portion may be connected to a scented liquid for absorption and the fan speed may be adjusted to vary the strength of the scent within the room.

SUMMARY

According to one aspect an air freshener system comprises a base, a reservoir, a coupling, and a filter. The base comprises a first base chamber, a second base chamber, a dividing floor partially separating the first base chamber from the second base chamber and comprising a fan opening. A majority of the fan is positioned within the second chamber adjacent the fan opening. A coupling receiver is positioned on an upper surface of the base adjacent the first chamber, and one or more base openings extend through a sidewall of the base, each base opening comprising an inlet opening in fluid communication with the first chamber and an outlet opening in fluid communication with the second chamber. The reservoir comprises a reservoir chamber configured to hold a scented liquid therein and an outlet. The coupling is coupled to the reservoir adjacent the outlet and configured to removably couple to the coupling receiver. The filter is coupled to the coupling and in fluid communication with the reservoir chamber, the filter being positioned above the fan when the coupling is removably coupled to the coupling and allowing the scented liquid to evaporate therefrom for dispersal through the outlet opening of the one or more base openings when the fan is activated.

Various implementations and embodiments may comprise one or more of the following. A valve assembly operably coupled to the coupling, the valve assembly adjustable within the coupling responsive to rotation of the coupling relative to the reservoir to increase or decrease an amount of scented oil in fluid communication with the filter. The filter may comprise a felt tip filter. The base may further comprise a third chamber adjacent the second chamber and opposite the first chamber, the third chamber comprising a circuit board positioned therein and operably coupled to the fan. A battery receptacle in the third chamber and operably coupled to the circuit board, wherein the fan is configured to be activated responsive to batteries mounted within the battery receptacle. An alternating current adapter positioned on the base and operably coupled to the circuit board, wherein the fan is configured to be activated responsive to an alternating current. A solar panel adjacent the reservoir and operably coupled to the circuit board, wherein the fan is configured for activation responsive solar power. An indicator on the coupling positioned to indicate the amount of scented oil in fluid communication with the filter.

According to another aspect, an air freshener system comprises a base, a reservoir, a coupling and a filter. The base comprises a fan housed therein, one or more base openings extending through a sidewall of the of the base and comprising an inlet opening and an outlet opening, and a coupling receiver positioned on an upper surface of the base. The reservoir comprises a reservoir chamber configured to hold a scented liquid therein and an outlet. The coupling is coupled to the reservoir adjacent the outlet and configured to removably couple to the coupling receiver. The filter is coupled to the coupling and in fluid communication with the reservoir chamber, the filter being positioned above the fan when the coupling is removably coupled to the coupling and allowing the scented liquid to evaporate therefrom for dispersal through the one or more base openings when the fan is activated.

Various implementations and embodiments may comprise one or more of the following. A valve assembly operably coupled to the coupling, the valve assembly adjustable within the coupling responsive to rotation of the coupling relative to the reservoir to increase or decrease an amount of scented oil in fluid communication with the filter. The base may further comprise a first base chamber, a second base chamber, and a dividing floor partially separating the first base chamber from the second base chamber and separating the inlet opening from the outlet opening of the one or more base openings, and comprising a fan opening, wherein the fan is positioned within the second chamber adjacent fan opening to draw air into the base through inlet opening of the one or more base openings and exhaust air through the outlet opening of the one or more base openings when activated. The filter may comprise a felt tip filter. The base may comprise a third chamber adjacent the second chamber and opposite the first chamber, the third chamber comprising a circuit board positioned therein and operably coupled to the fan. A battery receptacle in the third chamber and operably coupled to the circuit board, wherein the fan is configured to be activated responsive to batteries mounted within the battery receptacle. An alternating current adapter positioned on the base and operably coupled to the circuit board, wherein the fan is configured to be activated responsive to an alternating current. A solar panel adjacent the reservoir and operably coupled to the circuit board, wherein the fan is configured for activation responsive solar power. A marking on the coupling positioned to indicate the amount of scented oil in fluid communication with the filter.

According to another aspect, an air freshener system comprises a base and a chimney. The base comprises an air inlet, a fan housed within the base and positioned to draw air into the base through the air inlet upon activation of the fan, and a scent receptacle positioned adjacent the fan. The chimney is configured to removably couple to the base and comprises a plurality of ribs protruding from an inner surface of the chimney, the plurality of ribs positioned on the inner surface to created an airflow vortex within the chimney responsive to activation of the fan.

Various implementations and embodiments may comprise one or more of the following. The plurality of ribs may comprise a plurality of curved ribs positioned substantially equidistance from the adjacent rib of the plurality of ribs. The plurality of ribs may comprise a plurality of diagonal ribs positioned parallel to one another. A scented liquid inlet on either the chimney or the base and a scented liquid channel extending between the scented liquid inlet and the scent receptacle. The scent receptacle may comprise either a cylindrical shaped wick or a parabolic shaped wick. The scent receptacle may comprises a scent reservoir and a dispersion mechanism, the dispersion mechanism comprising one of a gas cartridge or an atomizing pump.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The invention will hereinafter be described in conjunction with the appended drawings, where like designations denote like elements, and.

DESCRIPTION

This disclosure, its aspects and implementations, are not limited to the specific components or assembly procedures disclosed herein. Many additional components and assembly procedures known in the art consistent with the intended air freshener and/or assembly procedures for an air freshener will become apparent for use with implementations of air fresheners from this disclosure. Accordingly, for example, although particular air fresheners disclosed, such air fresheners and implementing components may comprise any shape, size, style, type, model, version, measurement, concentration, material, quantity, and/or the like as is known in the art for such air fresheners and implementing components, consistent with the intended operation of an air freshener.

Various embodiments of the air fresheners disclosed herein provide improved systems, methods, and apparatus for holding and dispersing a scented liquid. In any of the embodiments described in this document, the scented liquid may comprise a scented oil. It is contemplated, however, the any other scented liquids may be adapted for use with the air fresheners disclosed herein.

Figure 1:
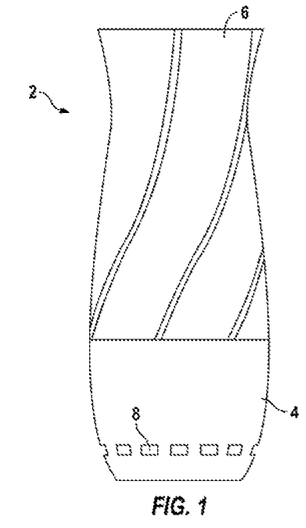
FIG. 1 is a side view of a first embodiment of an air freshener.
Figure 2A:
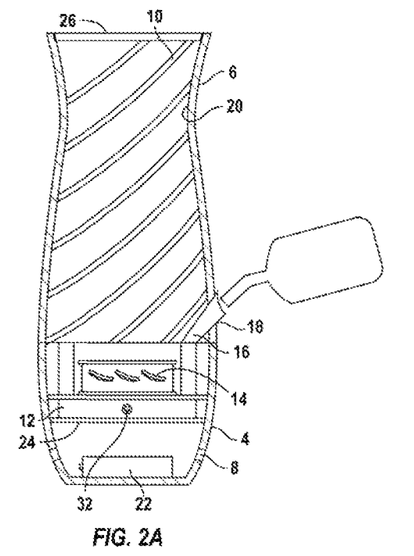
FIG. 2A is a partial cross-sectional view of the first embodiment of an air freshener that includes a first embodiment of a scent receptacle.

FIGS. 1 and 2 depict a particular embodiment of an air freshener 2. According to one or more aspects, an air freshener 2 comprises a base 4 and a chimney 6. The base 4 and the chimney 6 may be removably coupled, fixedly coupled, or integral with one another. In the particular embodiment depicted in FIGS. 1 and 2, the chimney 6 and the base 4 are removably coupled to one another.

In FIG. 2A, the chimney 6 and base 4 have been cross-sectioned for an internal view of an embodiment of an air freshener 2. Advantageous to conventional air fresheners, the chimney 6 of the air freshener depicted in FIG. 2A comprises a plurality of ribs 10 protruding from an inner surface 20 of the chimney 6. The plurality of ribs 10 are positioned on the inner surface 20 create an airflow vortex within the chimney 6 responsive to activation of the fan 14. The plurality of ribs 10 are, according to one aspect, ribs that are positioned substantially equidistance from the adjacent rib of the plurality of ribs 10. According to another aspect, the plurality of ribs 10 comprise a plurality of thin, parallel, diagonally positioned ribs extending in a spiral along an inside surface of the chimney 6. The depth of each rib may vary depending upon the vortex desired within the chimney 6, but in an embodiment with a 3 inch diameter chimney at its base, the depth of each rib may be between 0.25 inch and 0.6 inch so that the total depth of each rib is within a range of about $1/12$ to about $1/5$ of the diameter of the chimney 6 at its base where the airflow enters the chimney. In any case, the plurality of ribs 10 swirl airflow through the chimney 10 from the fan 14 and out through the chimney opening 26 to create an airflow vortex. The airflow vortex created by the plurality of ribs 10 is advantageous to conventional air fresheners because the vortex spreads the scented air from the air freshener outwardly more quickly than conventional air fresheners once the scented air is above the chimney 10.

In one or more embodiments, the base 4 comprises a fan 14 mounted and/or housed therein. The fan 14 may comprise any fan 14 known in the art and configured create the airflow vortex described above. In particular embodiments, the base comprises one or more air inlets 8 in the base 4. The one or more air inlets 8 are positioned to allow the fan 14 to draw air into the base 4 through the one or more air inlets 8 upon activation of the fan 14. Once the air as been drawn into the base 4 through the air inlets 8, the fan 14 exhaust the air through the chimney 6 as described above. In various embodiments the at least one fan 14 is powered by a power source such as a battery 22 or an alternating current.

In one or more embodiments, a scent receptacle is positioned within the base 4. The scent receptacle, according to various aspects, may be fixedly or removably coupled to the base 4. In the embodiment depicted in FIG. 2A, the scent receptacle is positioned below the fan 14. In other embodiments, however, the scent receptacle may be positioned above the fan 14. A mounting wall 24 is provided in typical embodiments for holding the scent receptacle thereon. The mounting wall 24 may comprise one or more holes that allow fluid communication between the fan 14 and the air inlets 8.

In the particular embodiment depicted in FIG. 2A, the scent receptacle comprises a reservoir 12 configured to hold scented liquid. The reservoir 12 may comprise a walled or bowl-like reservoir, or alternatively a capsule or bladder-like reservoir configured to hold the scented oil therein. In one or more embodiments, a dispersion mechanism 32 is operably coupled to the reservoir 12. The dispersion mechanism 32 is configured to disperse the scented liquid from the reservoir 12 towards the fan 14. According to various aspects, the dispersion mechanism 32 comprises a gas cartridge or atomizing pump spray. In various embodiments, the dispersion mechanism 32 is powered by a power source such as a battery.

Figure 2B:
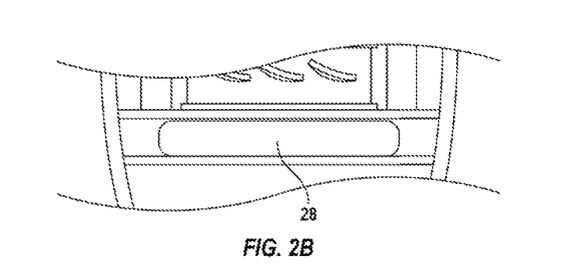
FIG. 2B is a partial view of the embodiment of FIG. 2A with a second embodiment of a scent receptacle.
Figure 2C:
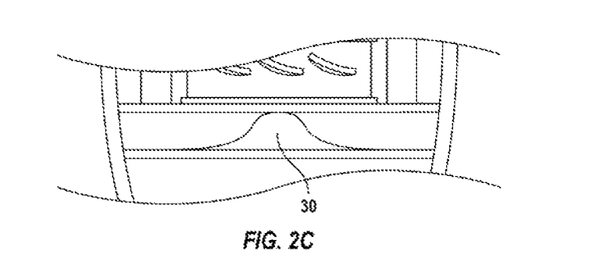
FIG. 2C is a partial view of the embodiment of FIG. 2A with a third embodiment of a scent receptacle.

FIGS. 2B and 2C depict other contemplated scent receptacles. In FIG. 2B, the scent receptacle comprises a cylindrical shaped wick 28. In FIG. 2C, the scent receptacle comprises a parabolic shaped wick 30. The cylindrical shaped wick 28 and the parabolic shaped wick 30 may are configured to retain the scented liquid and allow evaporation of the scent liquid from the respective wick 28, 30. The cylindrical shaped wick 28 and the parabolic shaped wick 30 may comprise any wick material previously known in the art.

Particular embodiments of an air freshener 2 comprise at least one scented liquid inlet 15 and a scented liquid channel 16 extending between the scented liquid inlet 15 and the scent receptacle 12, 28, 30. The at least one scented liquid inlet 15 and scented liquid channel 16 allow a user to add more scented liquid to the air freshener 2 without removal of either the scent receptacle 12, 28, 30 or the chimney 6.

Figure 3:
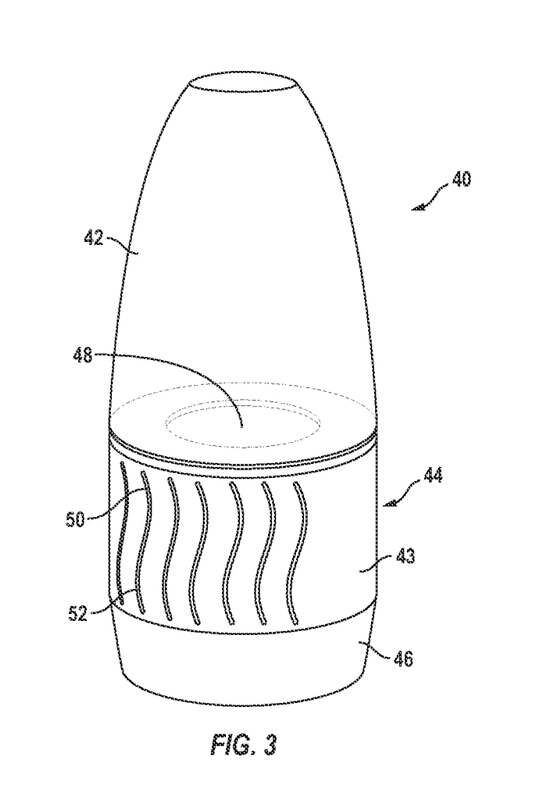
FIG. 3 is a perspective view of a second embodiment of an air freshener.
Figure 4:
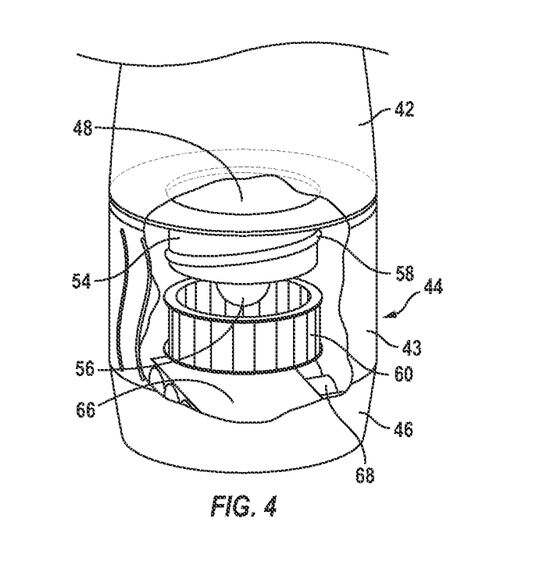
FIG. 4 is a perspective view of a second embodiment of an air freshener with a portion of the reservoir and base removed for internal viewing.
Figure 5:
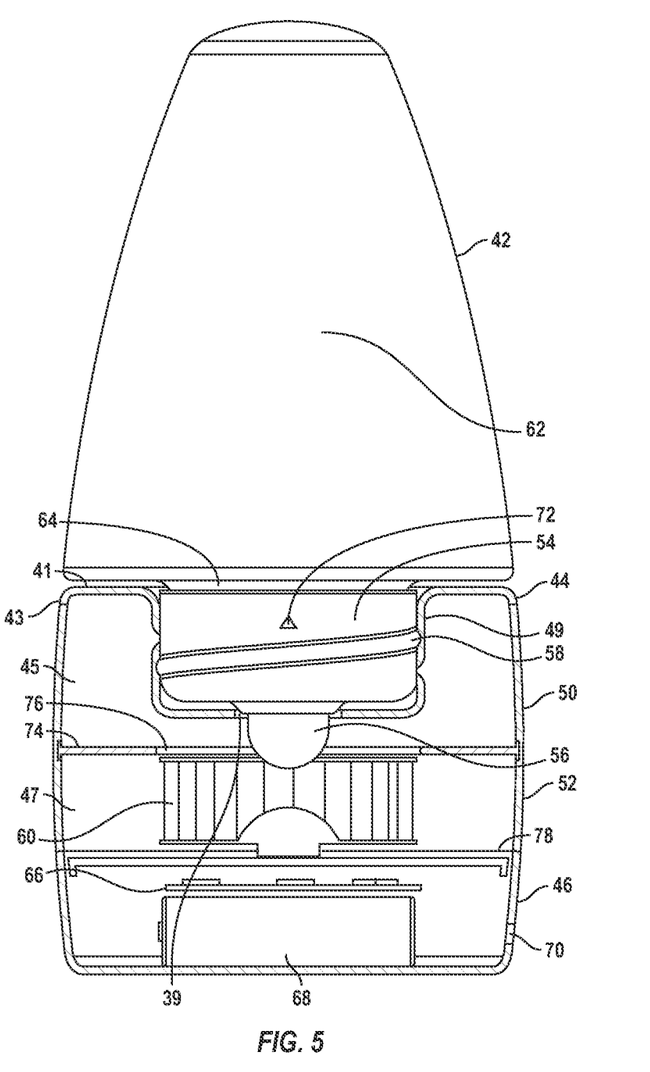
FIG. 5 is a partial cross-sectional view of the second embodiment of an air freshener.

FIGS. 3-5 depict another embodiment of an air freshener 40. One or more embodiments of an air freshener comprise a base 44, a reservoir 42, a coupling 54, and a filter 56. FIG. 3 depicts a perspective view of a non-limiting example of an air freshener that includes a reservoir 42 coupled to a base 44. The embodiment depicted in FIG. 3 also includes a chamber 46, although this chamber 46 is not required in all embodiments of the air freshener 40.

FIG. 5 depicts a partial cross-sectional view of an embodiment of an air freshener 40 with a portion of the base 44 of FIG. 3 removed for an internal view. In one or more embodiments, the base 44 comprises a first chamber 45 and a second chamber 47 adjacent the first chamber 45. A dividing floor 74 is positioned within the base 44 to partially separate the first chamber 45 and the second chamber 47. More particularly, one or more embodiments of the dividing floor 74 comprise a fan opening 76 extending through the dividing floor 74. The dividing floor 74 otherwise typically divides the first chamber 45 from the second chamber 47 between the fan opening 76 and the sidewall 43 of the base 44. In one or more embodiments, the dividing floor 74 is coupled to the sidewall 43 of the base 44.

The base 44 of various embodiments of an air freshener 40 further comprises one or more base openings extending through the sidewall 43 of the base 44. Each base opening is typically comprises an inlet opening 50 and an outlet opening 52. According to one aspect, the inlet opening 50 is positioned to allow fluid communication between the first chamber 45 and the air outside the air freshener 40, while the outlet opening 52 is positioned to allow fluid communication between the second chamber 47 and the air outside the air freshener 40. In certain embodiments, the inlet opening 50 and the outlet opening 52 comprise two separate openings. In other embodiments, such as the non-limiting example depicted in FIGS. 3-5, the inlet opening 50 and the outlet opening 52 comprise a single opening with the dividing floor 74 positioned at least partially between the inlet opening 50 and the outlet opening 52.

Embodiments of an air freshener 40 typically further comprise a fan 60 positioned within the second chamber 47 adjacent the fan opening 76. Alternatively, the fan 60 may be positioned within the first chamber 45 adjacent the fan opening 76. The fan 60 may comprise one or more of any fans known in the art and may also be mounted on a platform 78 that is either base of the second chamber 47 or the top of the third chamber 46. In operation, the fan 60 is positioned as such to draw air into the base 44 through the one or more inlet openings 50 and exhaust air through the one or more outlet openings 52 upon activation of the fan 60. Positioning of the fan 60 near or adjacent to the fan opening 76 of the dividing floor 74 enables the dividing floor 74 to form at least a partial seal between the first chamber 45 and the second chamber 47. This configuration, then, allow for more efficient air circulation through the base 44 of the air freshener 40 by maximizing the intake of the outside air through inlet opening 50 and exhausting scented air out of the base 44 through the outlet opening 52. The fan 60 is configured to be activated responsive to at least one of battery power, alternating current power, and/or solar power.

One more embodiments of a base 44 of an air freshener 40 further comprise a coupling receiver 49 positioned on an upper surface 41 of the base 44 adjacent the first chamber 45. The coupling receiver 49 typically extends either inward or outward from the first chamber 45 and is configured to couple to the coupling 54 of the reservoir 42. In the non-limiting embodiment depicted in FIG. 5, the coupling receiver 49 extends inward from the upper surface 41 of the base 44 and is configured to removably and threadedly couple to the coupling threads 58 of coupling 56. In other embodiments, the coupling 54 may simply rest in or about the coupling receiver 49. Particular embodiments of the coupling receiver 49 further comprise a filter opening 39 sized at least to allow the filter 56 of the reservoir 42 to extend therethrough.

Although not required in all embodiments, the base 44 of the non-limiting embodiment depicted in FIGS. 3-5 further comprises a third chamber 46 coupled to second chamber 47. The third chamber 46 may be removably coupled to the second chamber 47, fixedly coupled to the second chamber 47, or integral with the second chamber 47. In one or more embodiments, the third chamber 46 houses one or more batteries 68 configured to power the fan 60. The third chamber 46 may likewise house a circuit board 66 that is operably coupled to the fan 60 and the battery 68. Particularly embodiments further comprise an alternating current port 70 operatively coupled to the circuit board 66 and the fan 60, the alternating current port 70 configured to provide power to the fan 60 when an electrical cord is coupled thereto.

One or more embodiments of an air freshener 40 further comprise a reservoir 42. The reservoir 42 comprises a reservoir chamber 62 configured to hold a scented liquid therein. The reservoir 42 typically further comprises an outlet 64 or opening that allows fluid communication between the outside of the reservoir 42 and the reservoir chamber 62 unless the outlet 64 is otherwise plugged. In certain embodiments, the reservoir comprises a lip extending from the reservoir 42, the lip at least partially forming the boundary of the outlet 64. The reservoir 42 and reservoir chamber 62 may comprise any shape or configuration, including a shape that is flush with the sidewalls 43 of the base 44.

One or more embodiments of an air freshener 40 further comprise a coupling 54 coupled to the reservoir 42. The coupling 54 may be removably or fixedly coupled to the reservoir 42 at, for example, the lip of the reservoir 42 described above. In other embodiments, the coupling 54 is integral with the reservoir 42 an forms either a outward protrusion or inward chamber sized complementary to the coupling receiver 49 of the base 44. In one or more embodiments, the coupling 54 comprises one or more threads 58 that engage with the coupling receiver 49 for threaded engagement. The coupling may comprise plastic, rubber, metal, glass, or any other suitable material known in the art.

One or more embodiments of an air freshener 40 further comprise a filter 56. The filter 56 is typically in fluid communication with the reservoir chamber 62 unless prevented by the valve assembly 48. Thus, the filter is in fluid communication with scented liquid held within the reservoir chamber 62. The filter 56 may be fixedly or removably coupled to the coupling 54 or, alternatively, held in position due to the force of gravity. The filter 56 typically extends through or otherwise covers an opening in the coupling 54. In one or more embodiments, the filter 56 extends outwardly from the coupling 54 away from the reservoir 42.

FIG. 4 depicts an air freshener with a portion of the reservoir 42 and the sidewall 43 of the base 44 removed for internal viewing of the air freshener 40. The dividing floor 74 has also been removed in FIG. 4 to enable optimal viewing of the fan 60, filter 56, and coupling 54. According to one aspect, the filter 56 is positioned above and approximately central to the fan 60 of one or more embodiments. This positioning allows for maximum exposure of the filter 56 to air drawn into the base 44 upon activation by the fan 60 and, thus, maximum evaporation of scented liquid from the filter 56. In the non-limiting embodiment depicted in FIG. 5, the filter 56 extends from the coupling 54, through the filter opening 39 of the coupling receiver 49 into the first chamber 45, through the fan opening 76, and at least partially into the second chamber 47.

The filter 56 may comprise any filter known in the art. In one or more embodiments, the filter comprises a felt tip filter 56 that allows the scented liquid held in the reservoir chamber 62 to be exposed to the air inside the base 44 while simultaneously restricting the scented liquid from form large drops and dripping into the base 44. That is, the felt tip filter 56 allows the scented liquid to evaporate from the filter 56 without the scented liquid dripping off of the felt tip into the base 44.

One or more embodiments of an air freshener further comprise a valve assembly 48 configured to control the amount of fluid communication between the reservoir chamber 62 and the filter 56. In particular embodiments, the valve assembly 48 is operably coupled to the coupling 54 such that rotation of the coupling 54 in a first direction relative to the reservoir 42 generally increases the amount of fluid communication between the filter 56 and the reservoir chamber 62. This allows for a greater amount of scented liquid to saturate the filter 56, and thus a greater amount of evaporated scented oil for release. Rotation of the coupling 54 in a second direction opposite the first direction generally decreases the amount of fluid communication between the filter 56 and the reservoir chamber 62. In a particular embodiment, the coupling 54 comprises and indicator 72 such as an arrow that indicates the flow level of the scented liquid, or the amount of fluid communication between the reservoir chamber 62 and the filter 56.

The valve assembly 48 may comprise any assembly that allows for controlled fluid communication between the reservoir chamber 62 and the filter 56. In a particular, non-limiting example, the valve assembly 48 comprises two walls, each wall having at least one opening extending therethrough. In such an embodiment, a first wall remains in a fixed position while the second wall is rotatable, typically responsive to rotation of the coupling 54. When the openings of each of the first and second walls are fully aligned, fluid communication between the filter 56 and the reservoir chamber 62 is at a maximum. When openings of the each of the first and second walls are partially aligned or completely unaligned, fluid communication between the filter 56 and the reservoir chamber 62 is proportionally less or is completely blocked. The second wall may be rotated between the minimum and the maximum to allow fluid communication levels between the minimum and maximum as desired by the used. The two walls of the valve assembly 48 may be planar, or may be curved with an apex near the openings in particular embodiments to encourage gravitational fluid flow to the openings.

Figure 6:
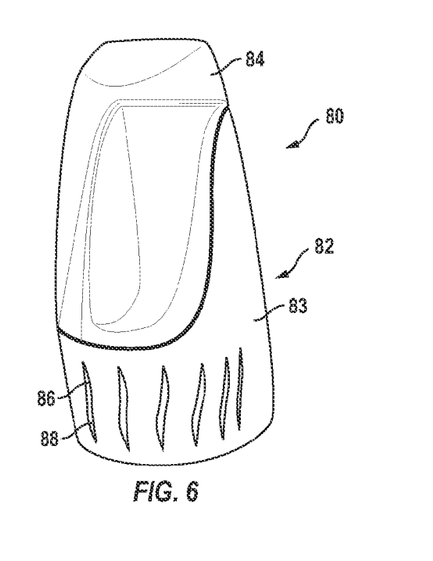
FIG. 6 is a front perspective view of a third embodiment of an air freshener.
Figure 7:
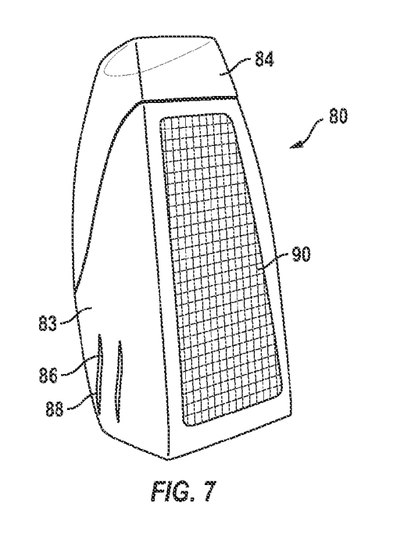
FIG. 7 is a rear perspective view of a third embodiment of an air freshener.
Figure 8:
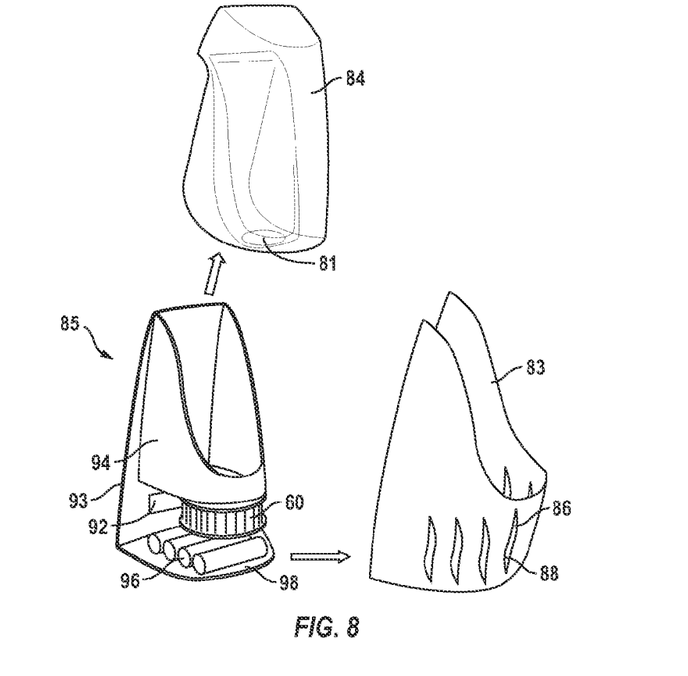
FIG. 8 is a break apart view of a third embodiment of an air freshener.

FIGS. 6-8 depict another non-limiting embodiment of an air freshener 80. In one or more embodiments, an air freshener 80 comprises a reservoir 84 and a base 82. The base 82 typically comprises a faceplate 83 removably coupled to a body 85. According to one, non-limiting embodiment, the faceplate 83 comprises a U-shaped faceplate 83 with one or more base openings extending therethrough. Similar to other embodiments, the base openings on the faceplate 83 may be divided into an inlet opening 86 and an outlet opening 88. In the particular embodiment depicted in FIGS. 6-8, the faceplate 83 comprises elongated sections on terminating ends of the faceplate 83, the elongated sections configured to reach the top of the body 85.

The body 85 of the base typically comprises a bottom wall 98, a sidewall 94 coupled to the bottom wall 98, and a mounting wall 94 coupled to the sidewall 93. The mounting wall 94 is typically positioned above the bottom wall 98. In a particular embodiment, the mounting wall 94 comprises a U-shaped mounting wall 94, with the terminating ends of the U-shaped mounting wall 94 being coupled to the sidewall 93. In other embodiments, the mounting wall 94 may comprise a plurality of separate mounting walls. The mounting wall 94 is configured to at least partially support the reservoir 84 when the reservoir 84 is mounted thereto.

According to one aspect, one or more chambers similar to the chambers described in relation to the air freshener 40 are formed in base 82 of the air freshener 80. For example, in one or more embodiments, at least two chambers are formed between the mounting wall 94 and the bottom wall 98, and between the sidewall 93 and the faceplate 83. In such an embodiment, a dividing floor may separate the two chambers and base openings as previously described in relation to other embodiments in this disclosure. A dividing wall may also comprise a fan opening similar to that previously described and be positioned within the base 82 to divide the air openings on the faceplate 83 into an inlet portion 86 and an outlet portion 88. In the particular embodiment depicted, the inlet portion 86 is above the outlet portion 88 of the openings. In other embodiments, however, the fan 60 is positioned such that the inlet portion 86 is below the outlet portion 88 depending upon how the fan is configured and oriented. The dividing wall, like that in FIG. 5 of a previous embodiment, is removed in FIG. 8 to more clearly illustrate the other components. The dividing wall may be formed around or adjacent to the fan, or as part of the faceplate 83. Scent oil may be transferred to the fan 60 through a felt tipped filter or other filter using the same structures as described in relation to the embodiment of FIGS. 3-5.

According to another aspect, one or more air outlet openings are positioned on the faceplate 83 as shown in FIG. 8, while one or more air inlet openings are positioned elsewhere on the air freshener 80. For example, in one or more embodiments, at least one air opening is disposed on wall extending from the reservoir 84. The wall extending from the reservoir 84 may comprise a sidewall or a top wall that allows the air inlet opening to be in fluid communication with the fan 60, while also coupling and/or support the reservoir to the base 82. In such embodiments, a channel is formed between the sidewall 93 of the base 82 and the reservoir 84, the channel allowing fluid communication between the air inlet openings and the fan 60. In other embodiments, one or more air inlet openings are disposed on the sidewall 93 of the base 82. In such embodiments, the air inlet openings extending through the sidewall 93 of the base 82 may be positioned adjacent the fan 60 or the reservoir 84 when the reservoir is mounted on the base 82.

One or more embodiments of an air freshener 80 further comprise a circuit board 92. The circuit board 92 may be coupled to the bottom wall 98, the sidewall 93, or the mounting wall 94. In the particular embodiment depicted in the break apart view of FIG. 8, the circuit board 92 is coupled to the sidewall 93. The air freshener 80 typically further comprises a battery mount 96 operably coupled to the circuit board 92 and/or the fan 60. In the particular embodiment depicted in FIG. 8, the battery mount 96 is coupled to the bottom wall 98. It is contemplated, however, that the battery mount 96 may be positioned anywhere on or in the air freshener 80.

One or more embodiments of an air freshener 80 further comprise a solar panel 90. The solar panel 90 is operably coupled to the circuit board 92 and/or the fan 60 and configured to provide power to the fan 60. In the particular embodiment depicted in FIG. 7, the solar panel 90 is positioned on the sidewall 93 opposite the mounting wall 94. In other embodiments, the solar panel 90 may be positioned on the faceplate 83 or the reservoir 84. The solar panel 90 may comprise any solar panel 90 known in the art and suitable for providing power to the fan 60.

The reservoir 84 is configured to removably couple to the mounting wall 94 and or the sidewall 93 of the body 85. In a particular embodiment, the reservoir 84 comprises one or more channels sized complementary to the mounting walls 94 such that the mounting wall fits within the channel and supports the reservoir 84. Additionally or alternatively, the reservoir 84 may comprise two walls positioned to hold the mounting wall between the two walls.

The reservoir 84 is also configured to hold a scented liquid therein. In particular embodiments, the reservoir have comprises an opening 81. The opening 81 is typically positioned such that it is above the fan 60 when the reservoir 84 is removably coupled to the base 82. Although not shown in detail in FIGS. 6-8, the air freshener 80 may further comprise a filter 56, a coupling 54, and/or a valve assembly 48 similar to those previously described in this document.

It will be understood that implementations are not limited to the specific components disclosed herein, as virtually any components consistent with the intended operation of a method and/or system implementation for an air freshener may be utilized. Accordingly, for example, although particular reservoirs, bases, fans, batteries, and solar panels may be disclosed, such components may comprise any shape, size, style, type, model, version, class, grade, measurement, concentration, material, weight, quantity, and/or the like consistent with the intended operation of a method and/or system implementation for an air freshener may be used.

In places where the description above refers to particular implementations of an air freshener, it should be readily apparent that a number of modifications may be made without departing from the spirit thereof and that these implementations may be applied to other air fresheners. The accompanying claims are intended to cover such modifications as would fall within the true spirit and scope of the disclosure set forth in this document. The presently disclosed implementations are, therefore, to be considered in all respects as illustrative and not restrictive, the scope of the disclosure being indicated by the appended claims rather than the foregoing description. All changes that come within the meaning of and range of equivalency of the claims are intended to be embraced therein.

The invention claimed is:

1. An air freshener system, comprising:
a base comprising a first base chamber, a second base chamber, a dividing floor partially separating the first base chamber from the second base chamber and comprising a fan opening, a majority of the fan positioned within the second chamber adjacent the fan opening, a coupling receiver positioned on an upper surface of the base adjacent the first chamber, and one or more base openings extending through a sidewall of the base, each base opening comprising an inlet opening in fluid communication with the first chamber and an outlet opening in fluid communication with the second chamber;
a reservoir comprising a reservoir chamber configured to hold a scented liquid therein and an outlet;
a coupling coupled to the reservoir adjacent the outlet and configured to removably couple to the coupling receiver;
a filter coupled to the coupling and in fluid communication with the reservoir chamber, the filter being positioned above the fan when the coupling is removably coupled to the coupling and allowing the scented liquid to evaporate therefrom for dispersal through the outlet opening of the one or more base openings when the fan is activated; and
a valve assembly operably coupled to the coupling, the valve assembly adjustable within the coupling responsive to rotation of the coupling relative to the reservoir to increase or decrease an amount of scented oil in fluid communication with the filter.

2. The air freshener system of claim 1, wherein the filter comprises a felt tip filter.

3. The air freshener system of claim 2, wherein the base further comprises a third chamber adjacent the second chamber and opposite the first chamber, the third chamber comprising a circuit board positioned therein and operably coupled to the fan.

4. The air freshener system of claim 3, further comprising an indicator on the coupling positioned to indicate the amount of scented oil in fluid communication with the filter.

5. The air freshener system of claim 3, further comprising a battery receptacle in the third chamber and operably coupled to the circuit board, wherein the fan is configured to be activated responsive to batteries mounted within the battery receptacle.

6. The air freshener system of claim 5, further comprising an alternating current adapter positioned on the base and operably coupled to the circuit board, wherein the fan is configured to be activated responsive to an alternating current.

7. The air freshener system of claim 6, further comprising a solar panel adjacent the reservoir and operably coupled to the circuit board, wherein the fan is configured for activation responsive solar power.

8. An air freshener system, comprising:
a base comprising a fan housed therein, one or more base openings extending through a sidewall of the base and comprising an inlet opening and an outlet opening, and a coupling receiver positioned on an upper surface of the base;

a reservoir comprising a reservoir chamber configured to hold a scented liquid therein and an outlet;

a coupling coupled to the reservoir adjacent the outlet and configured to removably couple to the coupling receiver;

a filter coupled to the coupling and in fluid communication with the reservoir chamber, the filter being positioned above the fan when the coupling is removably coupled to the coupling and allowing the scented liquid to evaporate therefrom for dispersal through the one or more base openings when the fan is activated; and a valve assembly operably coupled to the coupling, the valve assembly adjustable within the coupling responsive to rotation of the coupling relative to the reservoir to increase or decrease an amount of scented oil in fluid communication with the filter.

9. The air freshener system of claim 8, wherein the base further comprise a first base chamber, a second base chamber, and a dividing floor partially separating the first base chamber from the second base chamber and separating the inlet opening from the outlet opening of the one or more base openings, and comprising a fan opening, wherein the fan is positioned within the second chamber adjacent fan opening to draw air into the base through inlet opening of the one or more base openings and exhaust air through the outlet opening of the one or more base openings when activated.

10. The air freshener system of claim 9, wherein the filter comprises a felt tip filter.

11. The air freshener system of claim 10, wherein the base further comprises a third chamber adjacent the second chamber and opposite the first chamber, the third chamber comprising a circuit board positioned therein and operably coupled to the fan.

12. The air freshener system of claim 11, further comprising a marking on the coupling positioned to indicate the amount of scented oil in fluid communication with the filter.

13. The air freshener system of claim 11, further comprising a battery receptacle in the third chamber and operably coupled to the circuit board, wherein the fan is configured to be activated responsive to batteries mounted within the battery receptacle.

14. The air freshener system of claim 13, further comprising an alternating current adapter positioned on the base and operably coupled to the circuit board, wherein the fan is configured to be activated responsive to an alternating current.

15. The air freshener system of claim 14, further comprising a solar panel adjacent the reservoir and operably coupled to the circuit board, wherein the fan is configured for activation responsive solar power.

* * * * *